United States Patent [19]
Chipalkatti et al.

[11] Patent Number: 6,035,098
[45] Date of Patent: Mar. 7, 2000

[54] SCENT LAMP

[75] Inventors: Makarand H. Chipalkatti, Lexington; Frank St. Onge, Newburyport; Sharon Clement, Danvers; James Baker, Gardner; Keith Newfield, Tewksbury, all of Mass.; Denise Champagne, Atkinson, N.H.; Althea Cranton, Wenham, Mass.; Richard Comtois, Windham, N.H.; Keith Scott, Waldoboro; Steven McClenaghan, Ipswich, both of Mass.

[73] Assignee: Osram Sylvania Inc., Danvers, Mass.

[21] Appl. No.: 09/356,999

[22] Filed: Jul. 20, 1999

[51] Int. Cl.[7] .......................... A61M 16/00; A24F 25/00
[52] U.S. Cl. ............................................. 392/393; 239/53
[58] Field of Search .................................... 392/386, 390, 392/391, 392, 393–395; 239/53, 55, 56; 422/125, 126

[56] References Cited

U.S. PATENT DOCUMENTS

| | | | |
|---|---|---|---|
| 1,920,599 | 8/1933 | Schuh | 167/3 |
| 1,966,738 | 7/1934 | Seewagen | 219/45 |
| 1,988,617 | 1/1935 | Adams | 219/45 |
| 2,207,889 | 7/1940 | Kingman | 219/45 |
| 2,468,164 | 4/1949 | Brewster | 21/120 |
| 2,539,696 | 1/1951 | Morrison | 21/120 |
| 3,763,347 | 10/1973 | Whitaker | 219/275 |
| 4,145,001 | 3/1979 | Weyenberg et al. | 239/56 |
| 4,184,099 | 1/1980 | Lindaner et al. | 313/315 |
| 4,647,433 | 3/1987 | Spector | 422/125 |
| 4,965,490 | 10/1990 | Rabner | 313/569 |
| 5,109,029 | 4/1992 | Malone | 521/79 |

*Primary Examiner*—Sang Paik
*Attorney, Agent, or Firm*—William H. McNeill

[57] ABSTRACT

A scent-bearing ring adaptable for at least semi-permanent engagement with the neck of an incandescent bulb that generates both light and heat. The ring comprises an annular body having an inner layer formed to engage the bulb neck and an outer layer containing a scent or vapor-releasing agent actuable by heat. The inner layer is formed from a moldable material at least capable of resisting without substantial damage the heat generated by the bulb when the bulb is operated in a base-down position and capable of transferring the heat to the outer layer, the outer layer being moldable and porous.

11 Claims, 1 Drawing Sheet

SCENT LAMP

TECHNICAL FIELD

This invention relates generally to scent or vapor dispensing articles and more particularly to scent or vapor dispensing articles useable with conventional incandescent bulbs.

BACKGROUND ART

Various containers adaptable to incandescent bulbs for the purpose of dispensing vapors when heated have been often proposed. Of these, many have been designed to fit about the large or bulbous portion of the bulb, see, for example, U.S. Pat. Nos. 2,207,889; 3,763,347 and 4,184,099. Others have been designed to fit around the neck of the bulb, such as those shown in U.S. Pat. Nos. 1,920,599; 1,966,738; 1,988,616; 2,468,164; and 2,539,696. Still others have required the use of special bulbs, such as U.S. Pat. No. 4,965,490.

All of the previously proposed vapor dispensers have presented problems. For example, those that fit about the bulbous portion of the bulb obscure a material portion of the light emanating therefrom. Those that were designed to be fitted about the neck of the bulb often required that the bulb be used in a base-up position in order to keep the dispenser in position, or were difficult or expensive to manufacture.

DISCLOSURE OF INVENTION

It is, therefore, an object of the invention to obviate the disadvantages of the prior art. It is another object of the invention to enhance the usability of vapor dispensing articles.

Yet another object of the invention is the provision of a vapor dispenser for use with an incandescent bulb that fits securely and easily to the neck of the bulb.

Still another object of the invention is the provision of an article dispenser that is economical to manufacture.

These objects are accomplished, in one aspect if the invention, by a scent-bearing ring adaptable for at least semi-permanent engagement with the neck of an incandescent bulb which generates both light and heat, said ring comprising; an annular body having an inner layer formed to engage said bulb neck and an outer layer containing a scent or vapor releasing agent actuable by heat, said inner layer being formed from a moldable material at least capable of resisting without substantial damage the heat generated by said bulb when said bulb is operated in a base-down position and capable of transferring said heat to said outer layer, said outer layer being moldable and porous.

These objects are accomplished, in another aspect of the invention, by a scent-dispensing lamp having a source of light and heat with a body and a neck arranged along a longitudinal axis. The neck has at least one dimension smaller than that of the body, and terminates in a base. An annular scent-dispensing ring is semi-permanently fixed upon the neck above the base. The annular scent ring has an inner layer in contact with the neck and an outer layer. The inner layer is comprised of a heat resistant material and the outer layer is porous and contains a scent-releasing agent. Preferably, the inner layer is nylon and the outer layer is polypropylene.

In a preferred embodiment of the invention, the bottom of the scent ring is provided with a plurality of feet that engage the upper edge or surface of the base of the bulb to easily and semi-permanently retain the ring on the bulb. As used herein, "semipermanently" means retention through all normal uses of the bulb with ring attached. That is, the scent or vapor dispensing qualities of the ring is meant to approximate the life of the bulb; therefore, an occasion for removal of the ring should not arise.

Also, as used herein, the term "without substantial damage" means that the layers will not, during their useful life, sustain damage that would effect their function adversely.

In a still further embodiment of the invention, the moldable materials are electrically insulating, removing the hazards associated with some prior art vapor dispensers which employed metal bodies in proximity to the bulb base.

Thus, the invention obviates the disadvantages of the prior art. By fitting about the neck of the bulb it does not diminish the light output. It is held in place semi-permanently and thus allows the ring to sold attached to the bulb and allows the bulb to be burned base down. It is economical to manufacture, being a completely molded part with no extraneous manufacturing processes to raise the cost. And, it is formed of electrically insulating materials.

BEST MODE FOR CARRYING OUT THE INVENTION

For a better understanding of the present invention, together with other and further objects, advantages and capabilities thereof, reference is made to the following disclosure and appended claims taken in conjunction with the above-described drawings.

Figure 1:
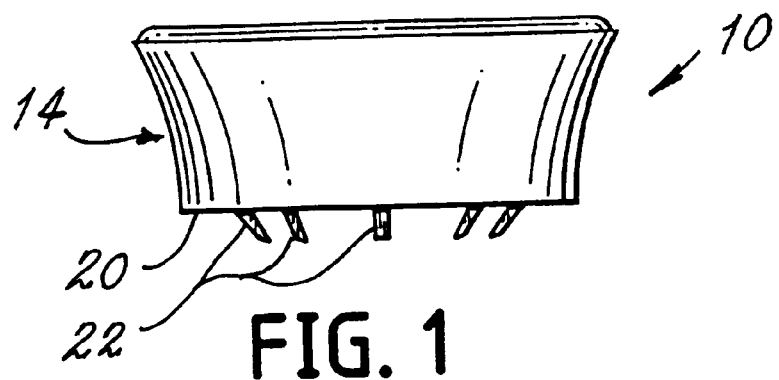
FIG. 1 is an elevational view of a scent or vapor dispensing ring in accordance with an aspect of the invention.

Referring now to the drawings with greater particularity, there is shown in FIG. 1 an annular scent-bearing ring 10 adaptable for at least semi-permanent engagement with the neck 11 of an incandescent bulb 12 which generates both light and heat. The ring comprises an annular body 14 having an inner layer 16 formed to engage the bulb neck 11 and an outer layer 18 containing a scent or vapor releasing agent actuable by heat. The inner layer 16 is formed from a moldable material at least capable of resisting without substantial damage the heat generated by the bulb 12 when it is operated in a base-down position. The material is capable of transferring heat to the outer layer 18, which outer layer is also moldable and porous. In a preferred embodiment of the invention the inner layer 16 is nylon and the outer layer 18 is polypropylene. Bulb 12 is preferably of the 60 to 100 watt variety. The 60 watt bulb under continuous operation will have a bulb wall temperature of about 150° C.; a 75 watt bulb about 150 to 180° C.; and a 100 watt bulb in the neighborhood of 200° C. Wattages greater than 100 watts are not recommended.

Figure 2:
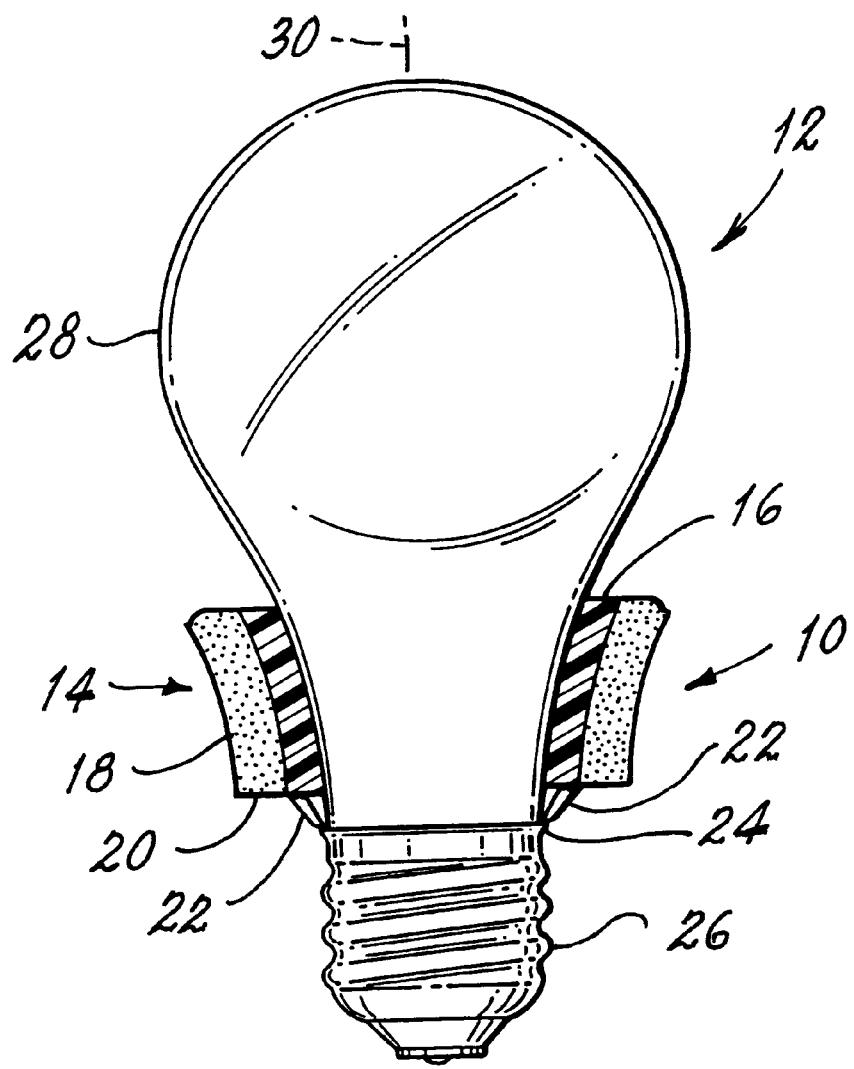
FIG. 2 is an elevational view of the ring mounted upon a bulb to form a scent or vapor lamp.

The body 14 of the ring 10 is preferably provided, on its lower edge 20, with a plurality of flexible feet or prongs 22. When placed on the neck 11 of a lamp 12 these prongs engage the slightly outwardly extending lip 24 of the lamp base 26, thereby retaining the ring 10 in position. As the feet 22 are formed as part of the non-electrically conductive inner layer 16, the potential for electrical shock is greatly minimized. As will be seen in FIG. 2, the neck 11 of the bulb 12 has a smaller dimension, i.e., diameter, than the main body portion 28 and both are arranged along a longitudinal axis 30. The type of bulb depicted is commonly referred to as an "A" line bulb. The vaporizable material can be any suitable material such as fragrances, e.g., vanilla (substituted benzaldehyde) or cinnamon (cinnamaldehyde, eugneol, and coumarin), or also, as is known in the art, various disinfectants, which are soluble in the polypropylene.

Thus, there is provided a scent ring and lamp bearing a scent ring that obviate the disadvantages of the prior art. The ring fits about the neck of the bulb and does not dramatically affect the light output. It is held in place semi-permanently, it is electrically insulating and it is cost effective to manufacture. Furthermore, the ring can be sold attached to the bulb as an integral part thereof. While there have been shown and described what are at present considered the preferred embodiments of the invention, it will be apparent to those skilled in the art that various changes and modifications can be made herein without departing from the scope of the invention as defined by the appended claims.

What is claimed is:

1. In a scent lamp having a source of light and heat with a body and a neck arranged along a longitudinal axis, said neck having at least one dimension smaller than said body and terminating in a base; and an annular scent ring semi-permanently fixed upon said neck above said base, the improvement comprising: said annular scent ring having an inner layer in contact with said neck and an outer layer, said inner layer being comprised of a heat resistant material and said outer layer being porous and containing a scent releasing agent, said inner layer being nylon and said outer layer being polypropylene.

2. The scent lamp of claim 1 wherein said source of light and heat is an incandescent bulb having a power consumption of about 60 to about 100 watts.

3. The scent lamp of claim 1 wherein said scent ring is molded.

4. The scent lamp of claim 2 wherein said scent releasing agent is present in an amount of about 10% to 25%, by weight, of said annular scent ring.

5. The scent lamp of claim 1 wherein said scent ring has an upper surface and a lower surface, said lower surface being adjacent the top portion of the base of said lamp and containing a plurality of feet engaging said top portion of said base.

6. The scent lamp of claim 1 wherein said annular scent ring frictionally engages said neck.

7. The scent lamp of claim 1 wherein said annular scent ring is adhesively fixed to said neck.

8. A scent-bearing ring adaptable for at least semi-permanent engagement with the neck of an incandescent bulb which generates both light and heat, said ring comprising; an annular body having an inner layer formed to engage said bulb neck and an outer layer containing a scent or vapor releasing agent actuable by heat, said inner layer being formed from a moldable material at least capable of resisting without substantial damage the heat generated by said bulb when said bulb is operated in a base-down position and capable of transferring said heat to said outer layer, said outer layer being moldable and porous.

9. The ring of claim 8 wherein said inner layer is nylon.

10. The ring of claim 8 wherein said outer layer is polypropylene.

11. The ring of claim 9 wherein said outer layer is polypropylene.

* * * * *